United States Patent [19]
Heuscher et al.

[11] Patent Number: 6,163,617
[45] Date of Patent: Dec. 19, 2000

[54] BACKPROJECTION WITH A MULTI-COLOR RENDERING ENGINE

[75] Inventors: Dominic J. Heuscher, Aurora; David D. Matthews, Twinsburg, both of Ohio

[73] Assignee: Picker International, Inc., Highland Heights, Ohio

[21] Appl. No.: 09/193,826

[22] Filed: Nov. 17, 1998

Related U.S. Application Data

[60] Provisional application No. 60/066,659, Nov. 26, 1997.

[51] Int. Cl.[7] .................................................. G06K 9/00
[52] U.S. Cl. ........................ 382/132; 382/279; 382/284; 382/162
[58] Field of Search .................................. 382/132, 162, 382/276, 279, 284; 378/4, 51, 86, 156; 430/967

[56] References Cited

U.S. PATENT DOCUMENTS

| | | | |
|---|---|---|---|
| 4,672,650 | 6/1987 | Masanobu | 378/4 |
| 5,008,822 | 4/1991 | Brunnett et al. | 600/425 |
| 5,293,312 | 3/1994 | Waggener | 378/14 |
| 5,481,583 | 1/1996 | Heuscher | 378/4 |

OTHER PUBLICATIONS

T.J. Cullip, et al. "Accelerating Volume Reconstruction with 3D Texture Hardware," UNC Tech Report TR93–27, May 1994.

B. Cabral, et al., "Accelerated Volume Rendering and Tomographic Reconstruction Using Texture Mapping Hardware."

S.G. Azevedo, "Model–Based Computed Tomography for Nondestructive Evaluation," Ph.D. Thesis Abstract, University of California, Davis, 1990.

*Primary Examiner*—Andrew W. Johns
*Assistant Examiner*—Shervin Nakhjavan
*Attorney, Agent, or Firm*—Fay, Sharpe, Fagan, Minnich & Mckee, LLP

[57] ABSTRACT

A method of diagnostic image reconstruction from projection data is provided. It includes generating projection data followed by a convolution of the same. The convolved projection data is then scaled into unsigned, fixed precision words of a predetermined number of bits. The words are then split into a predetermined number of color channels corresponding to color channels of a multi-color rendering engine (150). Simultaneously and independently, the split words are backprojected along each of the color channels to obtain backprojected views for each color channel. The backprojected views for each color channel are accumulated to produce separate color images corresponding to each color channel. Finally, the separate color images are recombined to produce an output image. In a preferred embodiment, prior to the convolution of the projection data, a rebinning operation is performed to ensure that the projection data is in a parallel format. In addition, after convolving the projection data, a selective pre-interpolating step of linear or higher order is optionally performed on the projection data.

20 Claims, 2 Drawing Sheets

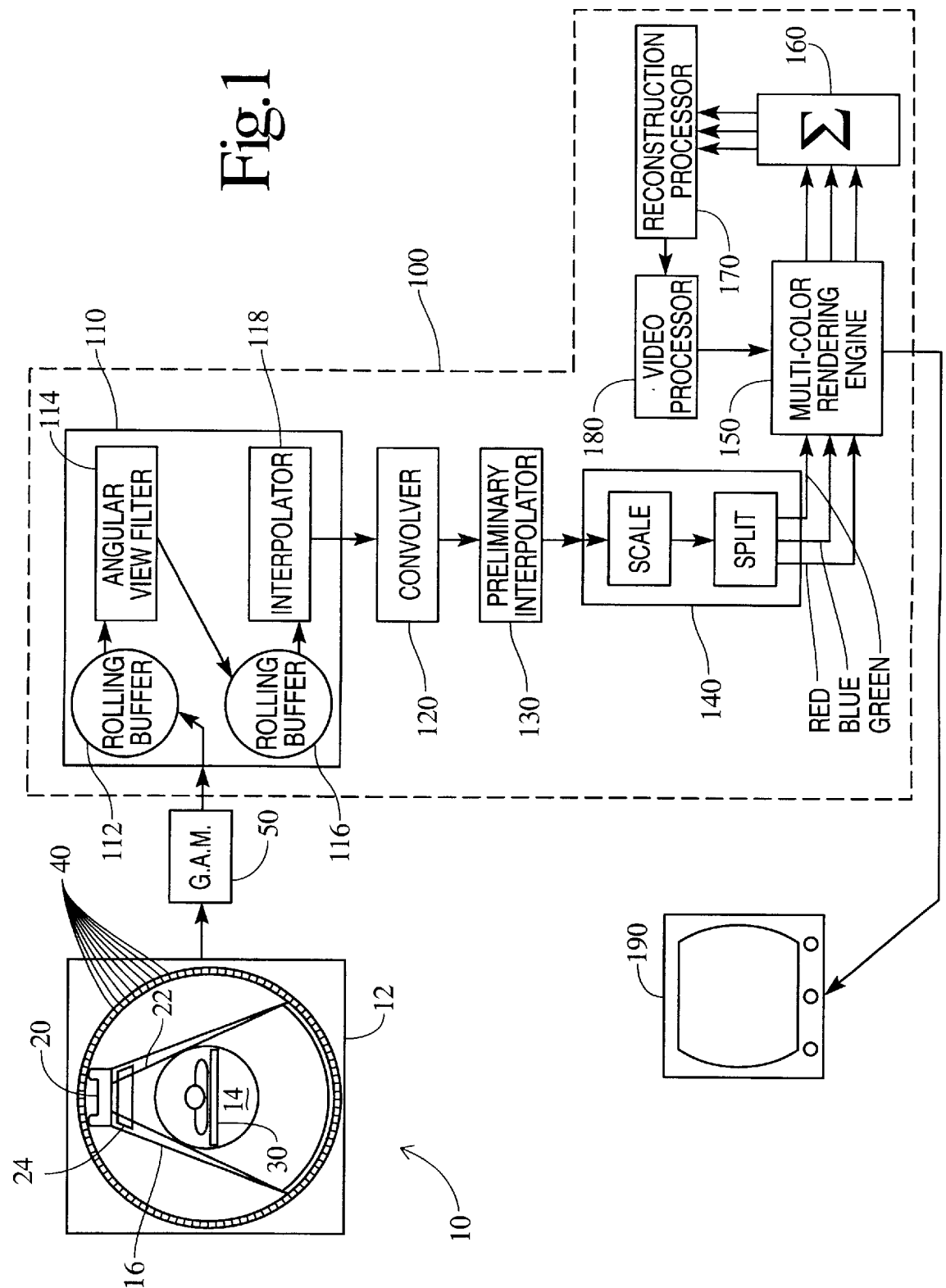

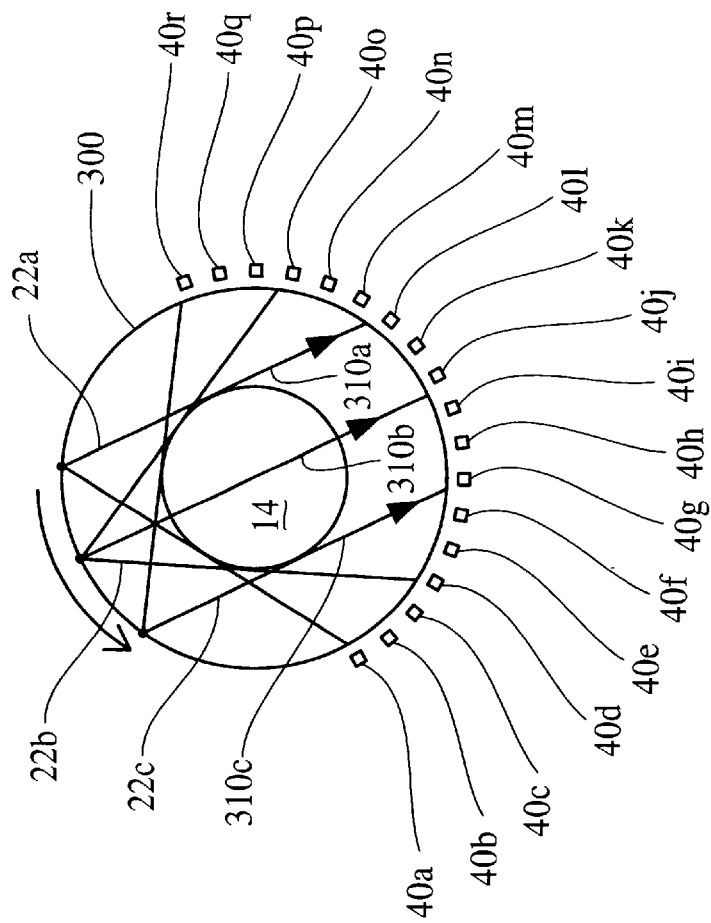
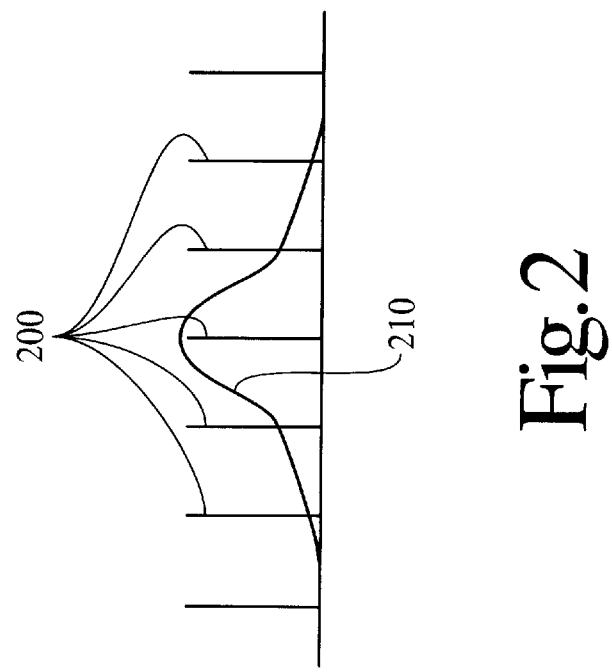
Fig.3
Fig.2

BACKPROJECTION WITH A MULTI-COLOR RENDERING ENGINE

This application claims the benefit of U.S. Provisional Application No. 60/066,659 filed Nov. 26, 1997.

BACKGROUND OF THE INVENTION

The present invention relates to the art of diagnostic medical imaging. It finds particular application in conjunction with CT scanners, and will be described with particular reference thereto. However, it is to be appreciated that the present invention is also amenable to other like applications which employ backprojectors in image reconstruction from projection data (e.g., nuclear cameras).

Generally, CT scanners have a defined examination region or scan circle in which a patient, phantom, or other like subject being imaged is disposed. A beam of radiation is transmitted across the examination region from an x-ray source to oppositely disposed radiation detectors. The segment of the beam impinging on a sampled detector defines a ray extending from the source to the sampled detector. The source, or beam of radiation, is rotated around the examination region such that data from a multiplicity of rays crisscrossing the examination region are collected. At given angular source positions about the examination region, a sampled view or data line is collected which represents the projection data for that view.

The sampled data is typically convolved and backprojected into an image memory commonly described as a two-dimensional array or matrix of memory elements. Each memory element stores a CT number indicative of the transmission or attenuation of the rays attributable to a corresponding incremental element within the examination region. The data from each ray which crossed the incremental element of the examination region contributes to the corresponding CT number, i.e., the CT number for each memory element of the resultant image is the sum of contributions from the multiplicity of rays which passed through the corresponding incremental element of the examination region.

Commonly, the x-ray data is transformed into the image representation utilizing filtered backprojection. A family of rays is assembled into a view. Each view is filtered or convolved with a filter function and backprojected into an image memory. Various view geometries have been utilized in this process. In one example, each view is composed of the data corresponding to rays passing parallel to each other through the examination region, such as from a traverse and rotate-type scanner. In a rotating fan-beam-type scanner, each view is made up of concurrent samplings of the detectors which span the x-ray beam when the x-ray source is in a given position, i.e., a source fan view. Alternately, a detector fan view is formed from the rays received by a single detector as the x-ray source passes behind the examination region opposite the detector.

Various backprojection algorithms have been developed. For CT scanners, it is generally advantageous to have the quickest display of the resultant CT images. In many applications, the many millions of computations required renders general purpose computers inappropriately slow for backprojection. To obtain the image representations, the backprojections are normally performed with dedicated backprojection hardware. Examples of such backprojection processors are described in commonly assigned, U.S. patent application Ser. No. 09/056,563 to John Sidoti et al., and U.S. Pat. No. 5,008,822 to Brunnett et al., both incorporated herein by reference. However, certain limitations of the described backprojection processors make them inappropriate for certain applications. One such limitation is the cost associated with dedicated and/or customized specialty hardware which, in turn, requires customized programming.

Other methods have also been previously developed which describe backprojection using rendering techniques. However, these methods tend to use an additional accumulation buffer and only utilize single color channels. In addition, zoom reconstruction with such systems includes modifying the backprojection hardware parameters in order to backproject a subset of the projection data. The problem is, however, that commonly used rendering hardware of limited precision does not always support the precision required for backprojection when only a single color channel is utilized. Moreover, an additional hardware accumulation buffer, not commonly found in rendering hardware, is also required to maintain backprojection accuracy if only a single color channel is utilized. Zoom reconstruction on such backprojection systems requires resetting the backprojection parameters in order to interpolate on a subset of the projection data. These factors limit the ease of use and accuracy of such backprojection techniques which utilize single color channels.

The present invention contemplates a new and improved backprojector and backprojection technique which overcomes the above-referenced problems and others.

SUMMARY OF THE INVENTION

In accordance with one aspect of the present invention, a method for diagnostic image reconstruction from projection data is provided. It includes generating projection data followed by a convolution of the same. The convolved projection data is then scaled into unsigned, fixed precision words of a predetermined number of bits. The words are then split into a predetermined number of color channels corresponding to color channels of a multi-color rendering engine. Simultaneously and independently, the split words are backprojected along each of the color channels to obtain backprojected views for each color channel. The backprojected views for each color channel are accumulated to produce separate color images corresponding to each color channel. Ultimately, the separate color images are recombined to produce an output image.

In accordance with a more limited aspect of the present invention, prior to the convolving step, the projection data is made parallel.

In accordance with a more limited aspect of the present invention, the parallel projection data is obtained by rebinning the generated projection data which was collected in a divergent fan-beam format.

In accordance with a more limited aspect of the present invention, the convolved projection data is selectively pre-interpolated prior to the scaling step.

In accordance with a more limited aspect of the present invention, the selective pre-interpolating includes a linear or higher order interpolation.

In accordance with a more limited aspect of the present invention, the simultaneous independent backprojections include a nearest neighbor interpolation.

In accordance with a more limited aspect of the present invention, the method further includes displaying the output image via the multi-color rendering engine.

In accordance with a more limited aspect of the present invention, at least some of the accumulating is performed in the multi-color rendering engine.

In accordance with a more limited aspect of the present invention, the accumulating performed in the multi-color rendering engine produces sub-images which are subsequently accumulated outside the multi-color rendering engine.

In accordance with another aspect of the present invention, an image processor is provided for use in connection with a diagnostic imaging apparatus that generates projection data. It includes a convolver which convolves angular views of the projection data from the diagnostic imaging apparatus. A data processor receives the convolved projection data, scales it into unsigned, fixed precision words of a predetermined bit length, and splits the words into multiple channels corresponding to separate colors. A multi-color rendering engine simultaneously and independently backprojects views along each separate color channel to generate corresponding images along each color channel. Ultimately, a reconstruction processor recombines the color channels into an output image.

One advantage of the present invention is that backprojection is performed efficiently on commonly available graphic hardware which is capable of multi-color rendering of objects.

Another advantage of the present invention is the reduction in overall system cost due to the fact that no customized backprojection hardware is employed to perform the backprojection.

Another advantage of the present invention is that accumulation of at least some views is accomplished in the multi-color rendering engine.

A further advantage of the present invention, which otherwise could be a limitation in a single color rendering algorithm, is that the precision of projection data and image data is maintained even when limited precision is available in the color rendering hardware.

Yet another advantage of the present invention is that zoom reconstruction is performed without resetting the backprojection parameters for each zoom region such that interpolation precision is maintained and the backprojector is simpler to construct and more efficient.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 1 is a diagrammatic illustration of a CT scanner system with backprojecting image processor in accordance with aspects of the present invention;

FIG. 2 is an exemplary illustration of the weighting function applied by the angular view filter in accordance with aspects of the present invention; and, FIG. 3 is a diagrammatic illustration showing the interpolation of data from a fan-beam format to a parallel-beam format in accordance with aspects of the present invention.

DETAILED DESCRIPTION OF THE PREFERRED EMBODIMENTS

With reference to FIG. 1, a CT scanner 10 includes a stationary gantry 12 which defines an examination region 14. A rotating gantry 16 is mounted on the stationary gantry 12 for rotation about the examination region 14. A source of penetrating radiation 20, such as an x-ray tube, is arranged on the rotating gantry 16 for rotation therewith. The source of penetrating radiation produces a beam of radiation 22 that passes through the examination region 14 as the rotating gantry 16 rotates. A collimator and shutter assembly 24 forms the beam of radiation 22 into a thin fan shape and selectively gates the beam 22 on and off. Alternately, the radiation beam 22 is gated on and off electronically at the source 20. In any event, a subject support 30, such as a couch or the like, suspends or otherwise holds a subject being examined or imaged at least partially within the examination region 14 such that the fan-shaped beam of radiation 22 cuts a cross-sectional slice through the region of interest of the subject.

Optionally, the subject is successively repositioned such that neighboring cross-sectional slices are taken in consecutive indexed fashion to produce a three-dimensional volume of slices. Alternately, as is the case with continuous spiral CT, concurrently with the rotation of the rotating gantry 16, the support 30, and consequently the subject thereon, are translated along a central horizontal axis of the examination region 14. In this manner, the source 20 follows a helical path relative to the subject. In another preferred embodiment, the support 30 remains stationary while the "stationary gantry" 12 is translated or otherwise moved relative to the subject such that the source 20 follows a helical path relative thereto.

In the illustrated fourth generation CT scanner, a ring of radiation detectors 40 is mounted peripherally around the examination region 14 on the stationary gantry 12. Alternately, a third generation CT scanner is employed with an arc of radiation detectors 40 mounted on the rotating gantry 16 on a side of the examination region 14 opposite the source 20 such that they span the arc defined by the fan-shaped beam of radiation 22. Regardless of the configuration, the radiation detectors 40 are arranged to receive the radiation emitted from the source 20 after it has traversed the examination region 14.

In a source fan geometry, an arc of detectors which span the radiation emanating from the source 20 are sampled concurrently at short time intervals as the source 20 rotates behind the examination region 14 to generate a source fan view. In a detector fan geometry, each detector is sampled a multiplicity of times as the source 20 rotates behind the examination region 14 to generate a detector fan view. The paths between the source 20 and each of the radiation detectors 40 are denoted as rays.

The radiation detectors 40 convert the detected radiation into electronic projection data. That is to say, each of the radiation detectors 40 produces an output signal which is proportional to an intensity of received radiation. Optionally, a reference detector may detect radiation which has not traversed the examination region 14. A difference between the magnitude of radiation received by the reference detector and each radiation detector 40 provides an indication of the amount of radiation attenuation along a corresponding ray of a sampled fan of radiation. In either case, each radiation detector 40 generates data elements which correspond to projections along each ray within the view. Each element of data in the data line is related to a line integral taken along its corresponding ray passing through the subject being reconstructed.

With detector view geometry, each view or data line represents a fan of rays having its apex at one of the radiation detectors 40 collected over a short period of time as the source 20 rotates behind the examination region 14 from the detector. With source view geometry, each view or data line represents a fan of rays having an apex at the source 20 collected by concurrent sampling of all the radiation detectors 40 spanning the fan of radiation.

A gantry acquisition memory board 50 receives the sampled data from the radiation detectors 40. The gantry acquisition memory board 50 optionally shuffles the data to transform it from a detector fan geometry to a source fan geometry, or vice versa, and performs a ripple filtering operation before passing the data to an image processor 100.

Optionally, for those applications wherein other than parallel projection data is collected, the image processor 100 includes a rebinning processor 110. The electronic data generated by the radiation detectors 40 and sampled by the gantry acquisition memory board 50 is fed to the rebinning processor 110. The rebinning processor 110 converts each data line from its fan-beam or otherwise divergent format to a parallel-beam format. In a preferred embodiment and in the interest of speed and accuracy, this process is optionally broken down into three rebinning operations or steps: an angular view filtering step, an interpolation step which sorts the data into unequally spaced parallel rays, and a final interpolative step that corrects for the unequal spacing of the rays. The rebinning processor 110 initially receives the data lines into a first rolling buffer 112. An angular view filter 114 retrieves the data lines from the first rolling buffer 112, filters them, and writes them into a preset position in a second rolling buffer 116. Additionally, any detector-specific corrections are optionally made prior to writing the data into the second rolling buffer 116. Preferably, as illustrated in FIG. 2, the angular view filter is applied across a plurality of adjacent data lines 200, for example 3 to 5, to generate a weighted average thereof. The weighted average is characterized by a centered symmetric non-linear function 210. Further, at this stage associated view reduction contributes to reduced processing time. Next, an interpolator 118 retrieves and reorders the data stored in the second rolling buffer 116 such that parallel rays from the various data lines are grouped together. Optionally, the number of data lines may be reduced by skipping data lines, for example, every other data line, in order to shorten the data processing time. Further, any corrections common to all the radiation detectors 40 are optionally made at this point. Next, an additional interpolative step is taken to equalize the spacing within each group of parallel data rays. Alternately, any appropriate rebinning processor is employed.

With reference to FIG. 3 and continuing reference to FIG. 1, an illustrative drawing showing a source fan geometry is useful for describing the rebinning process. As the source 20 follows a trajectory 300 around the examination region 14, it generates a plurality of source fan views 22*a–c* with each incremental degree of rotation. Each source fan view 22*a–c* is received by an array of radiation detectors 40*a–r* which converts it into a data line having a fan-beam format. The source fan views, 22*a–c* are each made up of a plurality of rays with each ray corresponding to an individual radiation detector 40*a–r*. For example, source fan view 22*a* includes rays corresponding to radiation detectors 40*a–l*, source fan view 22*b* includes rays corresponding to radiation detectors 40*d–o*, and 22*c* includes detectors 40*g–r*. The interpolator 118 reorders the data to group parallel rays, for example rays 310*a–c* which correspond to radiation detectors 40*l*, 40*j* and 40*g*, from respective fans 22*a*, 22*b* and 22*c* together to produce a parallel-beam format. Ultimately, the rebinning process simplifies the upcoming backprojection operation without compromising the image quality of the reconstructed image.

In any event, after parallel projection data has been obtained, it is fed to a convolver 120 which processes the view data and loads it into a preliminary interpolator 130. The convolver 120 performs mathematical manipulations which convolve each view with an appropriate filter or convolution function for the view format, namely parallel. It is noted that in a fourth generation scanner embodiment, as the source 20 moves, each of the radiation detectors 40 is concurrently generating intensity data. In order to accommodate this rapid flow of information, the convolver 120 preferably includes a plurality of convolvers for convolving several data lines concurrently.

The preliminary interpolator 130, receiving the convolved parallel projection data from the convolver 120, performs a linear or higher order interpolation on selected portions of each data line. In any event, the preliminary interpolator 130 performs a higher order interpolation than that used in the backprojection step in order to maintain interpolation precision during backprojection. Only that portion of the projection data defining the zoom reconstruction field (i.e., the particular region of interest upon which the reconstruction is to be focused) is interpolated and transferred to the backprojection step. The zooming is accomplished by selecting the appropriate portion of projection data for pre-interpolation. Preferably, no change in backprojection parameters is employed since parallel beam projections of constant size are being pre-interpolated. In a preferred embodiment, the preliminary interpolator 130 performs a mid-point interpolation with a cubic spline function to increase the data lines by a factor of two. Optionally, the pre-interpolation is carried out in accordance with the techniques taught in commonly assigned U.S. Pat. No. 5,481,583, incorporated herein by reference.

The preliminary interpolator then passes its output to a data processor 140 where the resulting pre-interpolated convolved parallel projection data is scaled and biased into unsigned fixed precision words of predetermined lengths. For exemplary purposes herein and in at least one preferred embodiment, the predetermined length of each word is 12 bits. However, other word lengths as are appropriate for various applications and/or levels of desired precision are also contemplated. The scaling and biasing involves determining a minimum and maximum floating point value and assigning those values to the minimum and maximum values of the 12 bit words (i.e., zero and 4095, respectively) with the intermediate floating point values being assigned relative to their location between the minimum and maximum floating point values.

In addition to scaling and biasing, the data processor 140 splits each word into multiple color channels corresponding to colors defined by a multi-color rendering engine 150. For exemplary purposes herein and in at least one preferred embodiment, the multi-color rendering engine 150 is a 24-bit three-color system with 8 bits per color channel. However, other multi-color rendering engines as are appropriate for various applications and/or levels of desired precision are also contemplated. Optionally, the division of colors on a 24-bit three-color system is defined using the following unsigned arithmetic wherein 'proj' is the 12-bit word:

$$red = proj/256 \quad (1);$$

$$green = (proj - 256 * red)/16 \quad (2);$$

and, $$blue = proj - 256 * red - 16 * green \quad (3);$$

wherein the choices for red, green, and blue are nominal and arbitrary. In this example then, red represents the four most significant bits, green the middle four significant bits, and blue the four least significant bits. The splitting is optionally accomplished via a hardware implementation of bit shifters, multipliers, and adders/subtractors. The data processor 140 is alternately implemented via an appropriate software application or combination of software and hardware.

This data is then transferred to the multi-color rendering engine 150 as 24-bit color texture map data. The multi-color rendering engine 150 is then employed to simultaneously and independently backproject the views or data lines along each of the color channels. To insure independence between channels, in a preferred embodiment, the backprojection operation is accomplished utilizing a nearest neighbor interpolation in the mapping of elements from the data line to the backprojection or image matrix. Hence, the projection data is rendered onto an image matrix, blending the results iteratively with the accumulated color images, one for each color channel. In a preferred embodiment, with 12-bit projection data (i.e., three 4-bit channels) and 8-bit color channels in the multi-color rendering engine 150, there are 4 extra bits per channel, and, therefore, the blended rendering operation can be iterated up to 16 times for 16 different views within the rendering engine 150 before any overflows occur. The resulting sub-image is then read out and a new sub-image is generated. If the rendering engine 150 and divided or split projection data are sized such that there is enough extra bits to accumulate all the views for a complete reconstructed image, then an external accumulation buffer 160 is not employed.

However if, for example, 50 sub-images or a total of 800 (16×50) views are used or desired to create a complete image, the sub-images that are read out of the rendering engine 150 get accumulated 50 times into the accumulation buffer 160 as a 16 or 32 bit by 3 color channel reconstructed image. Since this accumulation process takes over a magnitude less operations than the backprojection process itself, it adds very little to the overall backprojection time.

The multi-color images are then extracted from the accumulation buffer 160 and converted via a reconstruction processor 170 into a 16 or 32-bit image pixel-by-pixel using the following operations:

$$Output\_Image = Red\_Image * 256 + Green\_Image * 16 + Blue\_Image \quad (4).$$

Optionally, the reconstruction processor 170 is implemented as either a hardware, a software, or a combination of hardware and software configurations.

Alternately, the reconstruction processor 170 operates on the read out sub-images from the rendering engine 150 prior to their accumulation into the accumulation buffer 160 such that the multi-color sub-images are recombined into a single channel output sub-image via the operations from equation (4). The accumulation buffer 160 then accumulates the sub-images and stores them as the Output_Image.

In either case, the resulting image is then scaled and biased properly for image display. In a preferred embodiment, a video processor 180 withdraws and formats selected portions of the accumulated Output Image data to generate corresponding human-readable displays on a video monitor 190 or other rendering device. Typical displays include reprojections, selected slices or planes, surface renderings, and the like. Optionally, the rendering engine 150 is then also used to interpolate the data appropriately for the chosen display matrix size.

In this manner, backprojection is provided via use of graphic hardware commonly used to perform multi-color rendering of objects. The examples given illustrate how the multiple color channels of such a graphic device are used to perform backprojection and the advantages thereof. Zoom reconstruction with such a backprojection processor is also provided. In a preferred embodiment, unlike previous methods of performing zoom reconstruction on backprojection devices, no reconfiguration or changing of the backprojection parameters is performed. The examples given above are not to be interpreted as restricted to a particular hardware configuration, beam geometry, or by other steps employed in the reconstruction process. They are intended to illustrate the steps that permit use of a multi-color rendering engine for backprojection. Different combinations of precision of rendering hardware, projection data, and displayed image data are very applicable, perhaps using different scaling, bias, splitting, and accumulation of either projection data transferred into or images transferred out of the rendering engine 150. For example, a 64-bit rendering engine with 4 color channels (16 bits per channel) may be employed with projection data that is scaled into 16-bit words, or any other appropriate combination as desired for a given application or level of precision.

Moreover, where precision is not a concern or lower levels thereof are acceptable, the preliminary interpolator 130 is optionally omitted. The image processor 100 is also applicable to other diagnostic imaging apparatus. In a preferred alternate embodiment, a traverse and rotate type CT scanner provides parallel projection data. In another preferred alternate embodiment, a nuclear or gamma camera provides the projection data, in either a parallel or divergent format. Optionally, any appropriate diagnostic imaging apparatus which generates projection data is employed.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A method for diagnostic image reconstruction from projection data comprising:

(a) generating projection data;

(b) convolving the projection data;

(c) scaling the convolved projection data into unsigned fixed precision words of a predetermined number of bits;

(d) splitting the words into a predetermined number of color channels corresponding to color channels of a multi-color rendering engine;

(e) simultaneously and independently backprojecting the split words along each of the color channels to obtain backprojected views for each color channel;

(f) accumulating the backprojected views for each color channel to produce separate color images corresponding to each color channel; and, (g) recombining the separate color images to produce an output image.

2. The method according the claim 1, wherein prior to the convolving step the projection data is made parallel.

3. The method according to claim 2, wherein parallel projection data is obtained by rebinning the generated projection data which was collected in a divergent fan-beam format.

4. The method according to claim 1, wherein prior to the scaling step the convolved projection data is selectively pre-interpolated.

5. The method according to claim 4, wherein the selective pre-interpolating includes a linear or higher order interpolation.

6. The method according to claim 1, wherein the simultaneous independent backprojections include a nearest neighbor interpolation.

7. The method according to claim 6, wherein the accumulating performed in the multi-color rendering engine produces sub-images, which sub-images are subsequently accumulated outside the multi-color rendering engine.

8. The method according to claim 1, further comprising:

(h) displaying the output image via the multi-color rendering engine.

9. The method according to claim 1, wherein at least some of the accumulating is performed in the multi-color rendering engine.

10. An image processor for use in connection with a diagnostic imaging apparatus that generates projection data comprising:

a convolver which convolves angular views of the projection data from the diagnostic imaging apparatus;

a data processor which receives convolved projection data, scales it into unsigned fixed precision words of a predetermined bit length, and splits the words into multiple channels corresponding to separate colors;

a multi-color rendering engine which simultaneously and independently backprojects views along each separate color channel to generate corresponding images along each color channel; and, a reconstruction processor which recombines the color channels into an output image.

11. The image processor according to claim 10, further comprising:

a rebinning processor which receives and rebins the projection data from the diagnostic imaging apparatus into a parallel-beam format prior to passing it to the convolver.

12. The image processor according to claim 10, further comprising:

a preliminary interpolator which selectively interpolates convolved projection data from the convolver prior to passing it to the data processor.

13. The image processor according to claim 12, wherein the preliminary interpolator performs a linear or higher order interpolation.

14. The image processor according to claim 10, wherein the backprojection performed by the multi-color rendering engine includes a nearest neighbor interpolation.

15. The image processor according to claim 10, wherein the multi-color rendering engine accumulates a number of backprojected views for each separate color channel.

16. The image processor according to claim 15, wherein backprojected views accumulated by the multi-color rendering form sub-images for each separate color channel, which sub-images are read out and accumulated in an accumulator.

17. The image processor according to claim 16, wherein the sub-images from each color channel are recombined by the reconstruction processor prior to their accumulation in the accumulator such that the accumulation of recombined sub-images defines the output image.

18. The image processor according to claim 16, wherein the sub-images from each color channel are accumulated separately in the accumulator such that the separately accumulated sub-images are then recombined by the reconstruction processor to define the output image.

19. The image processor according to claim 10, further comprising:

an accumulator which accumulates backprojected views from the multi-color rendering engine.

20. The image processor according to claim 10, wherein the multi-color rendering engine is employed to interpolate the output image into a selected size display matrix.

* * * * *